(12) United States Patent
Imai

(10) Patent No.: US 11,051,786 B2
(45) Date of Patent: Jul. 6, 2021

(54) ACOUSTIC WAVE DIAGNOSTIC APPARATUS AND CONTROL METHOD THEREOF

(71) Applicant: FUJIFILM Corporation, Tokyo (JP)

(72) Inventor: Yoshiro Imai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 655 days.

(21) Appl. No.: 15/377,534

(22) Filed: Dec. 13, 2016

(65) Prior Publication Data

US 2017/0086784 A1 Mar. 30, 2017

Related U.S. Application Data

(63) Continuation of application No. PCT/JP2015/068342, filed on Jun. 25, 2015.

(30) Foreign Application Priority Data

Jul. 31, 2014 (JP) .............................. JP2014-156049

(51) Int. Cl.
*A61B 8/14* (2006.01)
*A61B 8/00* (2006.01)
(Continued)

(52) U.S. Cl.
CPC ................. *A61B 8/14* (2013.01); *A61B 8/06* (2013.01); *A61B 8/4254* (2013.01); *A61B 8/461* (2013.01);
(Continued)

(58) Field of Classification Search
CPC ......... A61B 8/488; A61B 8/5207; A61B 8/14; G01S 15/8988
See application file for complete search history.

(56) References Cited

U.S. PATENT DOCUMENTS 5,462,058 A 10/1995 Yamada et al.
5,570,691 A * 11/1996 Wright ................ G01S 7/52049
600/447

(Continued)

FOREIGN PATENT DOCUMENTS

JP 7-246205 A 9/1995
JP 7-303644 A 11/1995
(Continued)

OTHER PUBLICATIONS

International Search Report for PCT/JP2015/068342 (PCT/ISA/210) dated Sep. 29, 2015.
(Continued)

*Primary Examiner* — Keith M Raymond
*Assistant Examiner* — Milton Truong
(74) *Attorney, Agent, or Firm* — Birch, Stewart, Kolasch & Birch, LLP

(57) ABSTRACT

An acoustic wave diagnostic apparatus and control method processing for transmitting an ultrasound pulse converging on a focusing position in the same direction of a subject from acoustic wave transducers to be driven, among a plurality of ultrasound transducers included in an ultrasound probe, while sequentially updating the acoustic wave transducers to be driven is performed multiple times for the same ultrasound transducers. An acoustic wave echo signal group is obtained by receiving an ultrasound echo of an observation target position in the ultrasound transducers. An autocorrelation operation is performed on a signal, which is obtained by correcting the positional deviation of an acoustic wave echo signal group based on the positional deviation between the focusing position and the observation target position, and an ultrasound echo signal without positional deviation, and a Doppler shift signal indicating the speed of the observation target position is generated.

9 Claims, 13 Drawing Sheets

(51) Int. Cl.
*A61B 8/06* (2006.01)
*G01S 15/89* (2006.01)
*G01S 7/52* (2006.01)
*A61B 8/08* (2006.01)

(52) U.S. Cl.
CPC ............ *A61B 8/488* (2013.01); *A61B 8/5207* (2013.01); *G01S 7/52026* (2013.01); *G01S 15/8915* (2013.01); *G01S 15/8988* (2013.01)

(56) References Cited

U.S. PATENT DOCUMENTS

| | | | |
|---|---|---|---|
| 5,910,118 A * | 6/1999 | Kanda | G01S 15/8981 600/455 |
| 6,685,645 B1 | 2/2004 | McLaughlin et al. | |
| 2002/0151798 A1 * | 10/2002 | Honda | A61B 8/481 600/458 |
| 2008/0009727 A1 * | 1/2008 | Kataguchi | G01S 7/52085 600/437 |
| 2008/0030581 A1 * | 2/2008 | Johnson | G01S 7/52065 348/163 |
| 2009/0069693 A1 | 3/2009 | Burcher et al. | |
| 2009/0326377 A1 * | 12/2009 | Hirama | G01S 7/52046 600/447 |
| 2011/0237950 A1 * | 9/2011 | Meng | G01S 15/8909 600/447 |
| 2014/0371594 A1 * | 12/2014 | Flynn | A61B 8/463 600/454 |
| 2015/0141831 A1 | 5/2015 | Yamamoto | |
| 2015/0196280 A1 | 7/2015 | Yamamoto | |
| 2016/0120499 A1 | 5/2016 | Vignon et al. | |
| 2016/0174938 A1 * | 6/2016 | Takano | A61B 8/14 600/459 |

FOREIGN PATENT DOCUMENTS

| | | |
|---|---|---|
| JP | 10-99333 A | 4/1998 |
| JP | 2009-240700 A | 10/2009 |
| JP | 2009-536856 A | 10/2009 |
| JP | 2013-039388 A | 2/2013 |
| JP | 2013-525057 A | 6/2013 |
| JP | 2014-030715 A | 2/2014 |
| JP | 2014-079569 A | 5/2014 |

OTHER PUBLICATIONS

Written Opinion of the International Searching Authority for PCT/JP2015/068342 (PCT/ISA/237) dated Sep. 29, 2015.
Japanese Office Action dated Jun. 29, 2017, issued in corresponding Japanese patent application No. 2016-538223.

* cited by examiner

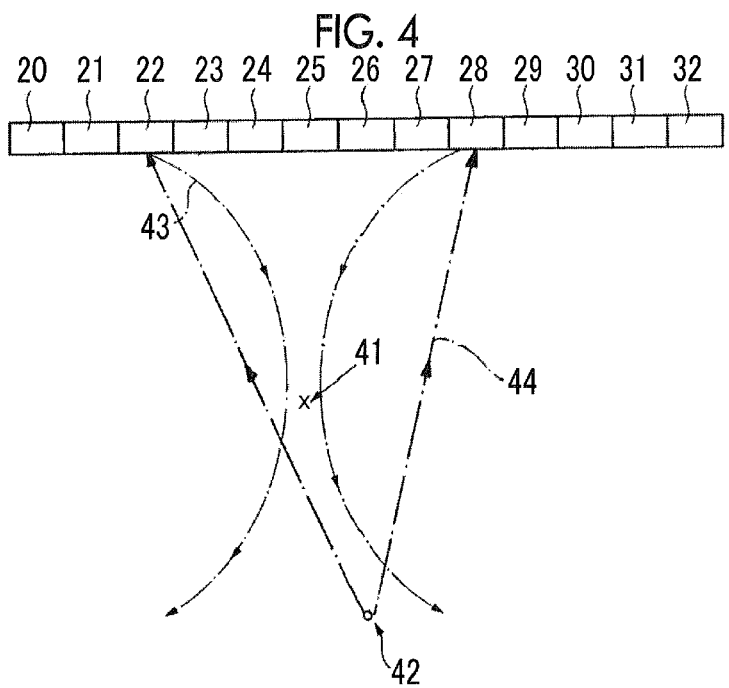
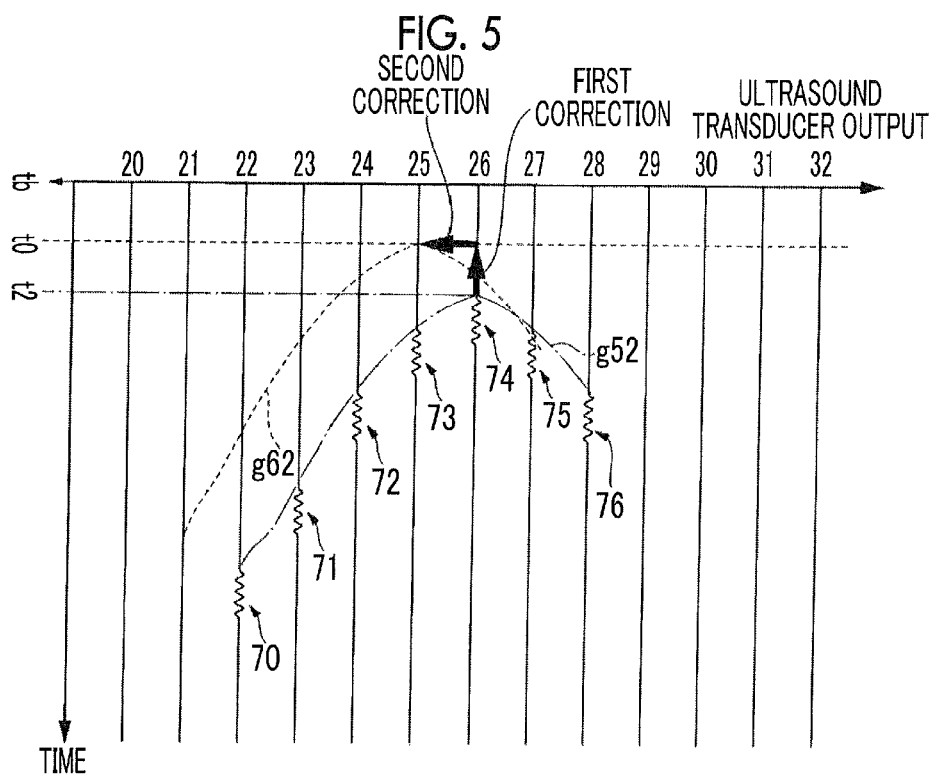

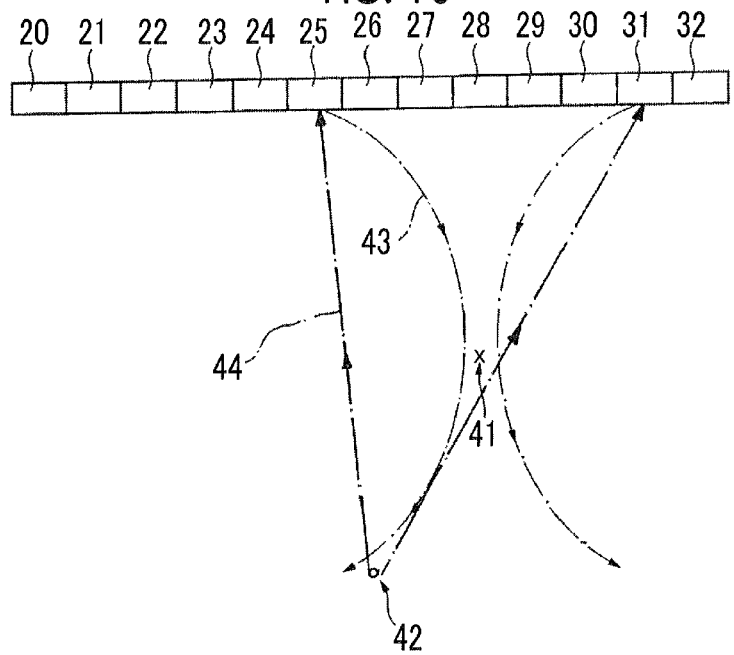
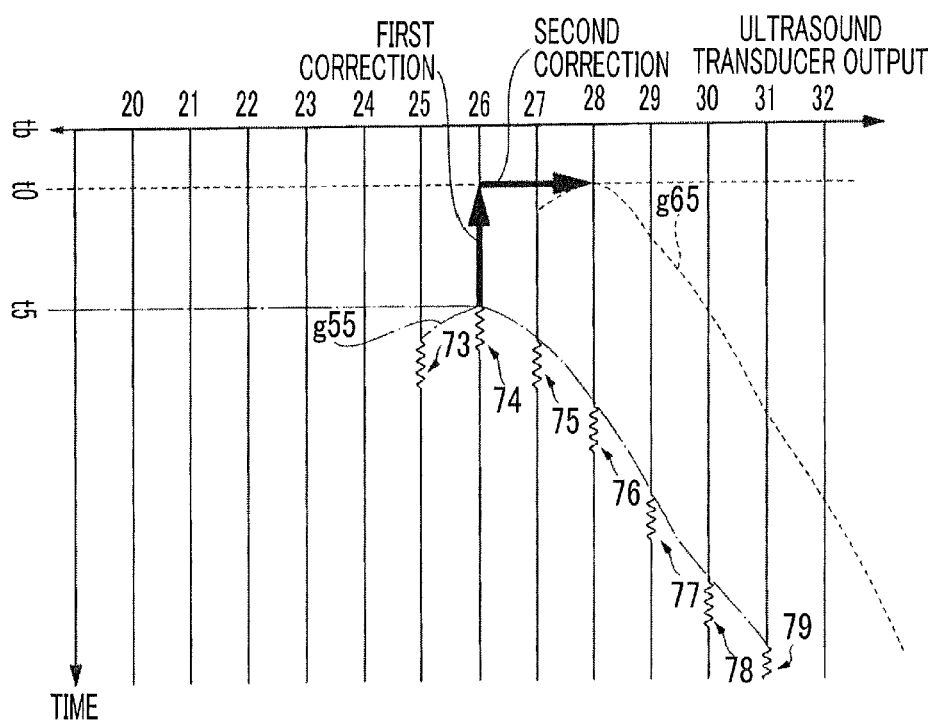

FIG. 18
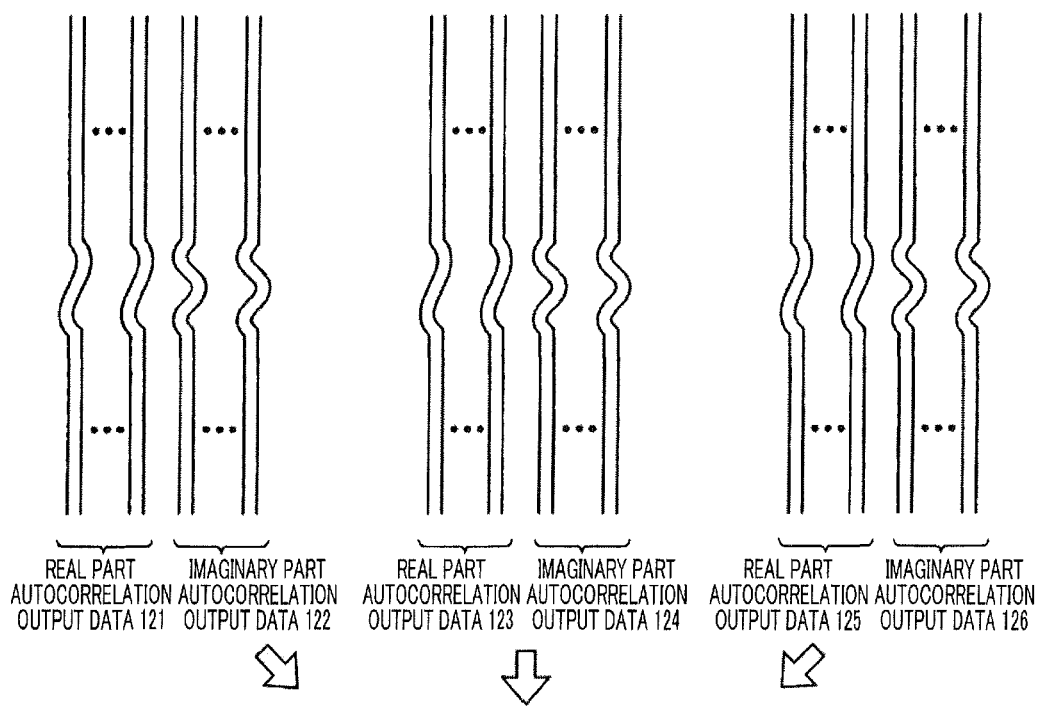
REAL PART          IMAGINARY PART     REAL PART          IMAGINARY PART     REAL PART          IMAGINARY PART
AUTOCORRELATION    AUTOCORRELATION    AUTOCORRELATION    AUTOCORRELATION    AUTOCORRELATION    AUTOCORRELATION
OUTPUT DATA 121    OUTPUT DATA 122    OUTPUT DATA 123    OUTPUT DATA 124    OUTPUT DATA 125    OUTPUT DATA 126
131
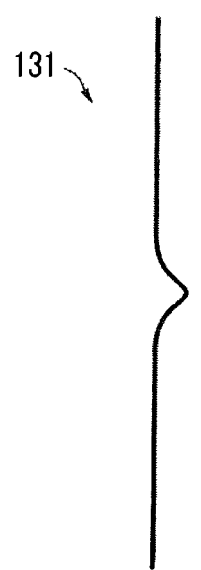

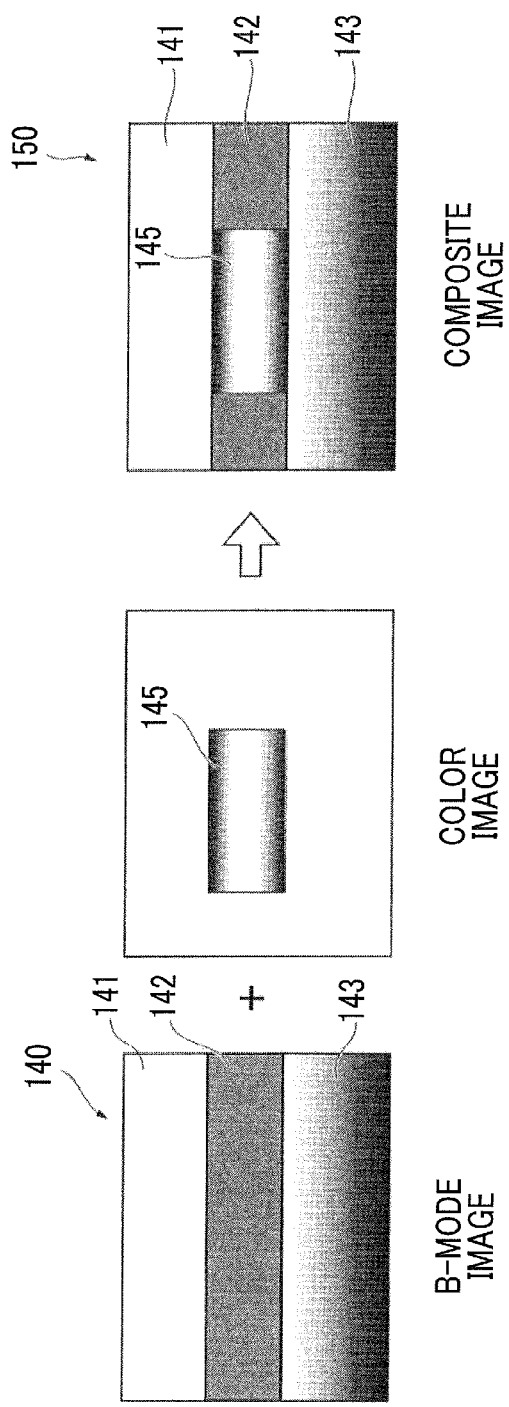

ACOUSTIC WAVE DIAGNOSTIC APPARATUS AND CONTROL METHOD THEREOF

CROSS-REFERENCE TO RELATED APPLICATIONS

This application is a Continuation of PCT International Application No. PCT/JP2015/068342 filed on Jun. 25, 2015, which claims priority under 35 U.S.C. § 119(a) to Japanese Patent Application No. 2014-156049 filed Jul. 31, 2014. Each of the above application(s) is hereby expressly incorporated by reference, in its entirety, into the present application.

BACKGROUND OF THE INVENTION

1. Field of the Invention

The present invention relates to an acoustic wave diagnostic apparatus and a control method thereof.

2. Description of the Related Art

In an ultrasound diagnostic apparatus, an image display method called a color mode (color flow mapping mode) is known. In the color mode, information (Doppler image) on the blood flow can be obtained based on the information of frequency shift due to the Doppler effect that is included in the ultrasound echo. A two-dimensional color image corresponding to the blood flow speed is generated from the obtained information, and is displayed after being combined with a B-mode image.

Techniques relevant to the ultrasound diagnostic apparatus include a tracking technique that works in an ultrasound imaging mode such as Doppler flow imaging (JP2013-525057A), a technique capable of forming a uniform beam width in the depth direction (JP2009-240700A), a technique of performing so-called multi-line processing (JP2014-079569A and JP2009-536856A), and the like. In addition, there is also a technique for a color Doppler imaging system (JP2013-039388A).

SUMMARY OF THE INVENTION

In the color mode, in order to ensure the sensitivity in the detection of the Doppler effect, transmission of ultrasound waves and reception of ultrasound echoes are normally repeated multiple times (about 4 to 16 times) at the same position (the same ultrasound transducer). Accordingly, the frame rate becomes lower than that in the case of the B mode. In particular, in a case where it is necessary to obtain a slow blood flow image, it is necessary to extend the interval of each transmission. Since this requires a time for obtaining the blood flow image, the frame rate is reduced to such an extent that a technician who operates the ultrasound diagnostic apparatus feels the stress.

JP2013-525057A is just for adjusting the focusing position of ultrasound waves, JP2009-240700A is intended to form a uniform beam width in the depth direction, and JP2014-079569A and JP2009-536856A are just for performing multi-line processing. In any of the above patent documents, obtaining a color tomographic image in a color mode has not been considered. In addition, although JP2013-039388A is relevant to the color Doppler imaging system, reducing the time until a color image (tomographic image) is obtained has not been considered at all.

It is an object of the present invention to reduce the time until a color image is obtained.

An acoustic wave diagnostic apparatus (ultrasound diagnostic apparatus) according to the present invention comprises: an acoustic wave probe in which a plurality of acoustic wave transducers are arranged in at least one direction; a driving device (driving means) for performing processing for transmitting acoustic waves, which converge on a focusing position, in the same direction of a subject from the acoustic wave transducers to be driven while sequentially updating the acoustic wave transducers to be driven; a positional deviation correction device (means positional deviation correction means) for correcting positional deviation according to a position of each of the acoustic wave transducers driven by the driving device, for an acoustic wave echo signal with positional deviation in the one direction between the focusing position and an observation target position of the subject among acoustic wave echo signals that are output from the acoustic wave transducers due to the acoustic wave transducers receiving acoustic wave echoes of the observation target position of the subject obtained based on the driving of the acoustic wave transducers by the driving device; and a Doppler operation device (Doppler operation means) for generating a Doppler shift signal by performing an autocorrelation operation on the acoustic wave echo signal, for which the positional deviation has been corrected by the positional deviation correction device, and the acoustic wave echo signal without the positional deviation.

The present invention may also provide a control method suitable for an acoustic wave diagnostic apparatus. That is, in a control method of an acoustic wave diagnostic apparatus comprising an acoustic wave probe in which a plurality of acoustic wave transducers are arranged in at least one direction, a driving device performs processing for transmitting acoustic waves, which converge on a focusing position, in the same direction of a subject from the acoustic wave transducers to be driven while sequentially updating the acoustic wave transducers to be driven, a positional deviation correction device corrects positional deviation according to a position of each of the acoustic wave transducers driven by the driving device, for an acoustic wave echo signal with positional deviation in the one direction between the focusing position and an observation target position of the subject among acoustic wave echo signals that are output from the acoustic wave transducers due to the acoustic wave transducers receiving acoustic wave echoes of the observation target position of the subject obtained based on the driving of the acoustic wave transducers by the driving device, a Doppler operation device generates a Doppler shift signal by performing an autocorrelation operation on the acoustic wave echo signal, for which the positional deviation has been corrected by the positional deviation correction device, and the acoustic wave echo signal without the positional deviation.

The driving device may perform the processing, which is for transmitting acoustic waves converging on the focusing position in the same direction of the subject from acoustic wave transducers to be driven while sequentially updating the acoustic wave transducers to be driven, multiple times. In this case, the Doppler operation device may generate a Doppler shift signal by performing an autocorrelation operation on a plurality of the acoustic wave echo signals, for which the positional deviation has been corrected by the positional deviation correction device, and a plurality of the acoustic wave echo signals without the positional deviation.

For example, the Doppler operation device may generate the Doppler shift signal from an average of an autocorrelation operation result of the plurality of acoustic wave echo signals, for which the positional deviation has been corrected by the positional deviation correction device, and an autocorrelation operation result of the plurality of acoustic wave echo signals without the positional deviation.

The Doppler operation device may generate the Doppler shift signal from a weighted average of an autocorrelation operation result of the plurality of acoustic wave echo signals, for which the positional deviation has been corrected by the positional deviation correction device, and an autocorrelation operation result of the plurality of acoustic wave echo signals without the positional deviation.

The Doppler operation device may generate the Doppler shift signal by increasing a weighting of the plurality of acoustic wave echo signals without the positional deviation and calculating a weighted average of an autocorrelation operation result of the plurality of acoustic wave echo signals, for which the positional deviation has been corrected by the positional deviation correction device, and an autocorrelation operation result of the plurality of acoustic wave echo signals without the positional deviation.

The Doppler operation device may generate the Doppler shift signal by performing an autocorrelation operation on each of the plurality of acoustic wave echo signals without the positional deviation and the plurality of acoustic wave echo signals, for which the positional deviation has been corrected by the positional deviation correction device, among the plurality of acoustic wave echo signals with the smallest positional deviation.

The acoustic wave diagnostic apparatus may further comprise a delay time correction device for correcting a time difference between transmission of the acoustic waves by the acoustic wave transducers and reception of the acoustic wave echoes by the acoustic wave transducers, which occurs based on positions of the acoustic wave transducers in the acoustic wave probe. In this case, the Doppler operation device may generate the Doppler shift signal for the acoustic wave echo signal for which a delay time has been corrected by the delay time correction device, for example.

According to the present invention, processing for transmitting acoustic waves, which converge on the focusing position, in the same direction of the subject from the acoustic wave transducers while sequentially updating the driving of the acoustic wave transducers arranged in the acoustic wave probe is performed. Then, acoustic wave echoes of the observation target position of the subject are received by the acoustic wave transducers, so that acoustic wave echo signals are obtained. For the acoustic wave echo signal with positional deviation in one direction between the focusing position and the observation target position, positional deviation is corrected. A Doppler shift signal is generated by performing an autocorrelation operation on the acoustic wave echo signal, for which positional deviation has been corrected, and the acoustic wave echo signal without positional deviation. A color image is generated from the Doppler shift signal. Since the acoustic wave echo signals for which positional deviation has been corrected are used, it is possible to reduce the number of times to transmit acoustic waves to the subject from the acoustic wave transducers compared with a case of generating the Doppler shift signal using only a plurality of acoustic wave echo signals without positional deviation. As a result, it is possible to reduce the time until a color image is generated.

BRIEF DESCRIPTION OF THE DRAWINGS

FIG. 4 shows the transmission of ultrasound pulses and the reception of ultrasound echoes.

FIG. 5 shows an ultrasound echo signal.

FIG. 10 shows the transmission of ultrasound pulses and the reception of ultrasound echoes.

FIG. 11 shows an ultrasound echo signal.

FIG. 18 shows autocorrelation data and data indicating a Doppler frequency.

FIG. 20 shows how a composite image is generated from a B-mode image and a color-mode image.

DESCRIPTION OF THE PREFERRED EMBODIMENTS

Figure 1:
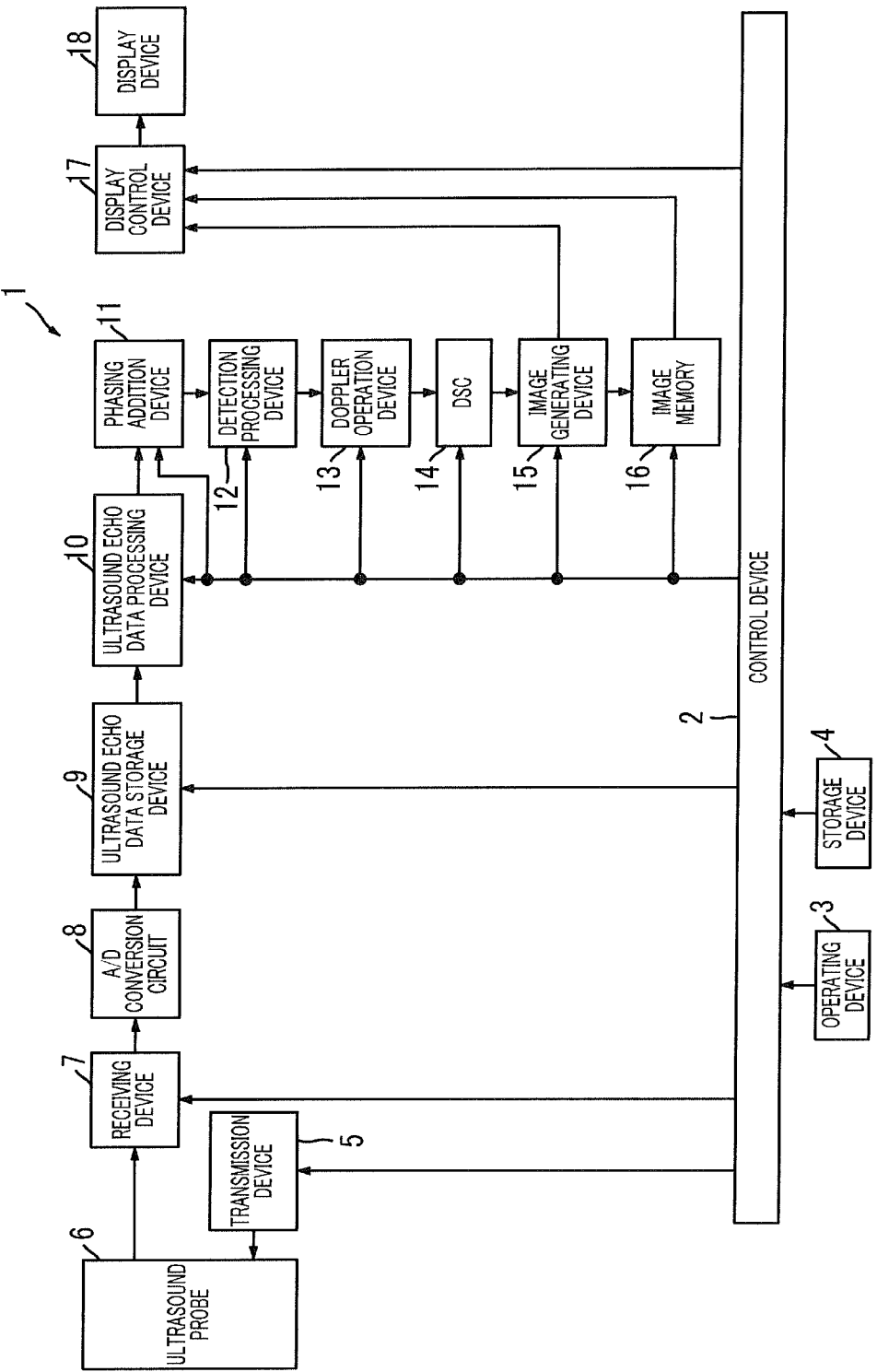
FIG. 1 is a block diagram showing the electrical configuration of an ultrasound diagnostic apparatus.

FIG. 1 shows an embodiment of the present invention, and is a block diagram showing the electrical configuration of an ultrasound diagnostic apparatus (acoustic wave diagnostic apparatus).

In the present embodiment, an ultrasound wave is used as an acoustic wave. However, as long as an appropriate frequency is selected according to an object to be examined, measurement conditions, and the like, an acoustic wave having an audible frequency may be used without being limited to the ultrasound wave. In the ultrasound diagnostic apparatus in the present embodiment, it is possible to obtain a B-mode image, a color image, and a composite image (image obtained by combining the B-mode image and the color image). First, a processing in a case where a color image is obtained will be described.

The overall operation of an ultrasound diagnostic apparatus 1 is controlled by a control device 2.

An operating device 3, which is operated by a technician or the like who operates the ultrasound diagnostic apparatus 1, and a storage device 4, in which predetermined data and the like are stored, are connected to the control device 2.

An ultrasound probe 6 is included in the ultrasound diagnostic apparatus 1. A plurality of ultrasound transducers are included in the ultrasound probe 6.

A control signal output from the control device 2 is supplied to a transmission device 5. Then, an electrical pulse is supplied to each ultrasound transducer of the ultrasound probe 6 from the transmission device 5. The electrical pulse is converted into an ultrasound pulse by the ultrasound transducer, the ultrasound pulse propagates through the body of a subject, and the ultrasound echo returns to the ultrasound probe 6.

The ultrasound echo is converted into an electrical signal (ultrasound echo signal) by the ultrasound transducer.

FIGS. 2 to 11 show a state in which an ultrasound pulse is output from the ultrasound probe 6 and an ultrasound echo signal is obtained.

Figure 2:
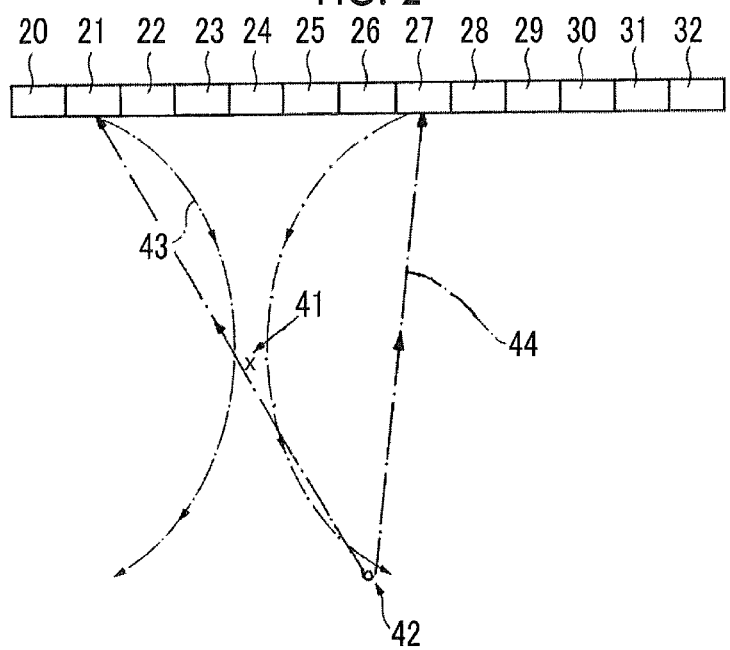
FIG. 2 shows the transmission of ultrasound waves and the reception of ultrasound echoes.
Figure 6:
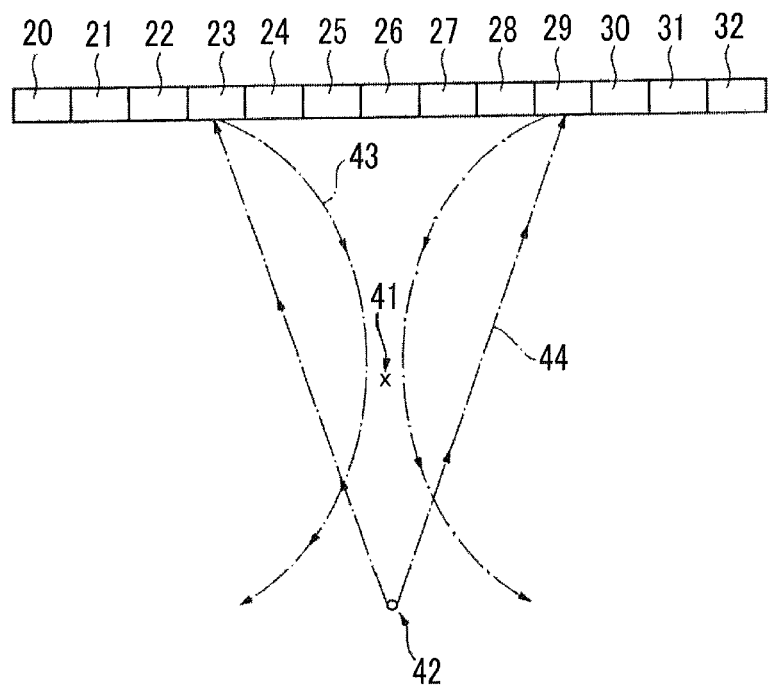
FIG. 6 shows the transmission of ultrasound pulses and the reception of ultrasound echoes.
Figure 8:
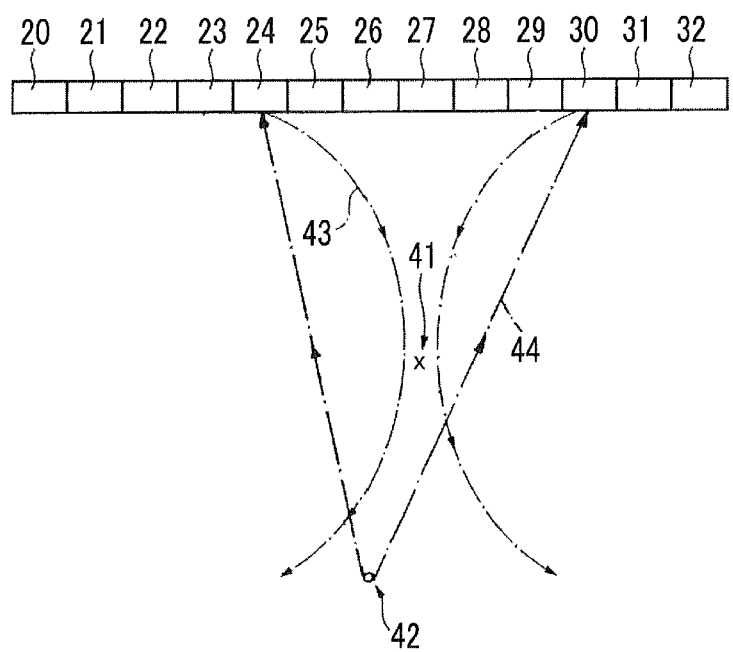
FIG. 8 shows the transmission of ultrasound pulses and the reception of ultrasound echoes.

FIG. 2 shows a state in which an ultrasound pulse 43 is output from ultrasound transducers 21 to 27 among ultrasound transducers 20 to 32 included in the ultrasound probe 6. FIG. 4 shows a state in which the ultrasound pulse 43 is output from the ultrasound transducers 22 to 28 among the ultrasound transducers 20 to 32 included in the ultrasound probe 6. FIG. 6 shows a state in which the ultrasound pulse 43 is output from the ultrasound transducers 23 to 29 among the ultrasound transducers 20 to 32 included in the ultrasound probe 6. FIG. 8 shows a state in which the ultrasound pulse 43 is output from the ultrasound transducers 24 to 30 among the ultrasound transducers 20 to 32 included in the ultrasound probe 6. FIG. 10 shows a state in which the ultrasound pulse 43 is output from the ultrasound transducers 25 to 31 among the ultrasound transducers 20 to 32 included in the ultrasound probe 6.

Thus, a plurality of ultrasound transducers (acoustic wave transducers) 20 to 32 arranged in at least one direction (or in a two-dimensional manner) are included in the ultrasound probe 6. By the control device 2 (a driving device), an ultrasound pulse (acoustic wave) 43 converging on the focusing position 41 is transmitted from ultrasound transducers to be driven while the ultrasound transducers to be driven, among the ultrasound transducers 20 to 32, are being updated in a sequential manner (while the ultrasound transducers to be driven are being changed in a sequential manner). Preferably, as will be described later, in order to accurately obtain a color image of the color mode indicating the blood flow speed in a subject, the control device 2 (a driving device) controls the ultrasound transducers 20 to 32 so that processing for transmitting the ultrasound pulse to the observation target position 42 present inside the subject is performed multiple times.

Referring to FIG. 6, it is assumed that the ultrasound pulse 43 is transmitted from the ultrasound transducers 23 to 29. The ultrasound pulse 43 is transmitted from the ultrasound transducers 23 to 29 so as to converge on the focusing position 41 at a predetermined distance in the transmission direction of the ultrasound transducer 26 (in FIG. 2, directly below the ultrasound transducer 26) located at the center of the ultrasound transducers 23 to 29. Since the ultrasound pulse 43 is transmitted with a delay according to the positions of the ultrasound transducers 23 to 29, the ultrasound pulse 43 converges on the focusing position 41. In the example shown in FIG. 6, the observation target position 42 (for example, a position where the medium changes in the subject) is present in the extension direction of the central ultrasound transducer 26 and the focusing position 41. For this reason, the ultrasound pulse 43 is emitted to the observation target position 42, and an ultrasound echo 44 is generated from the observation target position 42. The ultrasound echo 44 is received by the ultrasound transducers 23 to 29.

Figure 7:
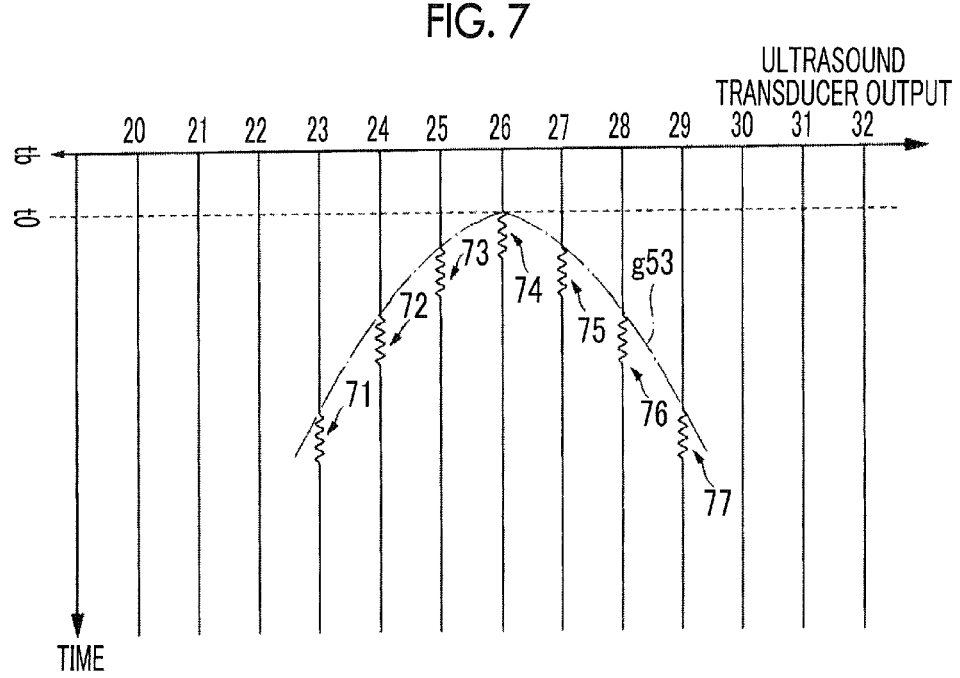
FIG. 7 shows an ultrasound echo signal.

FIG. 7 shows ultrasound echo signals 71 to 77 output from the ultrasound transducers 23 to 29 that have received the ultrasound echo 44. The horizontal axis indicates the position of the ultrasound transducer, and the vertical axis indicates the elapsed time from a time tb at which the ultrasound pulse 43 is output from the ultrasound transducer.

Since a difference between the propagation distances of the ultrasound pulse 43 and the ultrasound echo 44 occurs according to the positions of the ultrasound transducers 23 to 29, the output timing of the ultrasound echo signals 71 to 77 output from the ultrasound transducers 23 to 29 also differs depending on each ultrasound transducer. The propagation distance of the ultrasound pulse 43 output from the central ultrasound transducer 26 and the propagation distance of the ultrasound echo 44 of the central ultrasound transducer 26 from the observation target position 42 are the shortest. Accordingly, the ultrasound echo signal 74 is first output from the central ultrasound transducer 26 (time t0). The propagation distance of the ultrasound pulse 43 output from the ultrasound transducers 25 and 27 on both sides of the central ultrasound transducer 26 and the propagation distance of the ultrasound echo 44 of the ultrasound transducers 25 and 27 from the observation target position 42 are the second shortest. Accordingly, the ultrasound echo signals 73 and 75 are output from the ultrasound transducers 25 and 27 after the ultrasound echo signal 74. Similarly, the ultrasound echo signals 72 and 76 are then output from the ultrasound transducers 24 and 28. Finally, the ultrasound echo signals 71 and 77 are output from the ultrasound transducers 23 and 29. In FIG. 7 (the same for other diagrams), in order to show the ultrasound echo signals 71 to 77, an envelope of the ultrasound echo signals 71 to 77 is shown as an ultrasound echo signal group g53.

Referring to FIG. 2, it is assumed that the ultrasound pulse 43 is transmitted from the ultrasound transducers 21 to 27. If the ultrasound pulse 43 converges on the focusing position 41 and does not spread exceeding the width of one ultrasound transducer (in the case shown in FIG. 2, the ultrasound transducer 24), the ultrasound pulse 43 is not emitted to the observation target position 42 (for example, a position where the medium changes in the subject), which is not present in the extension direction of the central ultrasound transducer 24, among the ultrasound transducers 21 to 27 that transmit ultrasound waves, and the focusing position 41. Accordingly, no ultrasound echo 44 is generated from the observation target position 42. However, since the ultrasound pulse 43 spreads when the ultrasound pulse 43 passes the focusing position 41, the ultrasound pulse 43 is also emitted to the observation target position 42 that is not present in the extension direction of the central ultrasound transducer 24 and the focusing position 41. Accordingly, the ultrasound echo 44 is generated from the observation target position 42. The ultrasound echo 44 is received by the ultrasound transducers 21 to 27.

Figure 3:
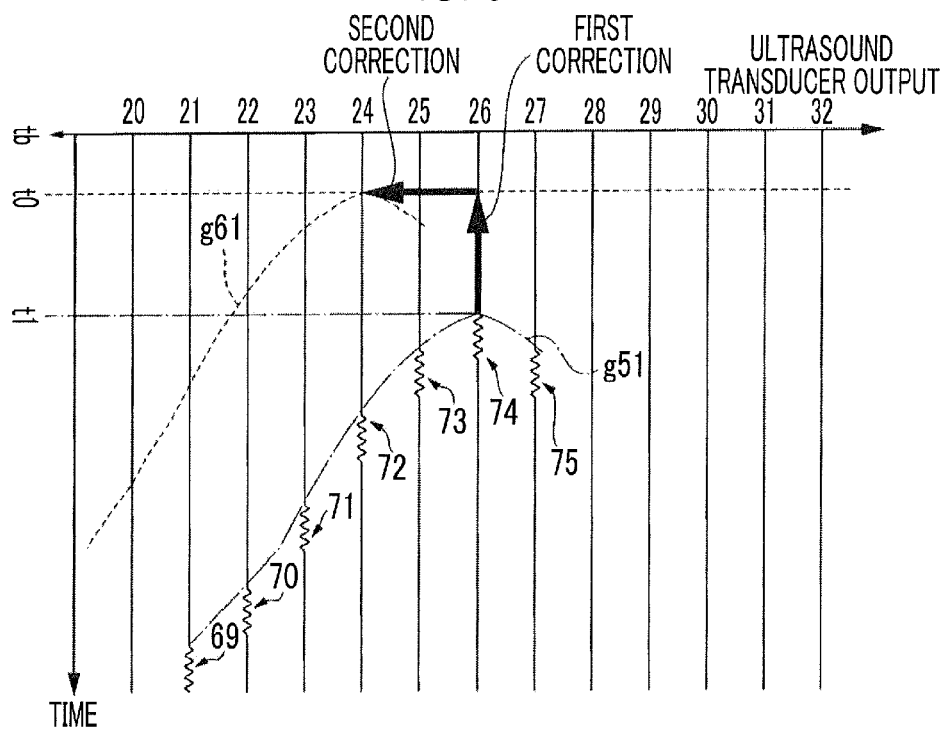
FIG. 3 shows an ultrasound echo signal.

FIG. 3 shows an ultrasound echo signal group g51 output from the ultrasound transducers 21 to 27 that receive the ultrasound echo 44. As shown in FIG. 7, the ultrasound echo signal group g51 is an envelope of ultrasound echo signals 69 to 75 output from the ultrasound transducers 21 to 27. Since the observation target position 42 is present in the output direction (in FIG. 2, directly below) of the ultrasound pulse 43 of the ultrasound transducer 26 among the ultrasound transducers 21 to 27 that receive the ultrasound echo 44, the ultrasound echo signal 74 is first output from the ultrasound transducer 26 (time t1). Then, the ultrasound echo signals 73 and 75 are output from the ultrasound transducers 25 and 27, respectively, and then the ultrasound echo signal 72 is output from the ultrasound transducer 24. In addition, the ultrasound echo signal 71 is output from the ultrasound transducer 23, the ultrasound echo signal 70 is output from the ultrasound transducer 22, and the ultrasound echo signal 69 is output from the ultrasound transducer 21. Since the focusing position 41 is not present between the observation target position 42 and the ultrasound transducer 26 that receives the ultrasound echo 44, the time t1 at which the ultrasound echo signal 74 is first output as shown in FIG. 3 is later than the time t0 at which the ultrasound echo signal 74 is first output as shown in FIG. 7.

Referring to FIG. 4, it is assumed that ultrasound transducers to be driven are updated and the ultrasound pulse 43 is transmitted from the ultrasound transducers 22 to 28. In the same manner as described with reference to FIG. 2, the ultrasound echo 44 from the observation target position 42 is received by the ultrasound transducers 22 to 28.

Referring to FIG. 5, an ultrasound echo signal group g52 is obtained from the ultrasound transducers 22 to 28 in the same manner as in FIG. 3. As shown in FIG. 7, the ultrasound echo signal group g52 is also an envelope of ultrasound echo signals 70 to 76 output from the ultrasound transducers 22 to 28. The ultrasound echo signal 74 is first output from the ultrasound transducer 26 (time t2).

When ultrasound transducers to be driven are updated and the ultrasound pulse 43 is transmitted from the ultrasound transducers 23 to 29 as shown in FIG. 6, the operation is the same as that already described.

Referring to FIG. 8, it is assumed that ultrasound transducers to be driven are updated and the ultrasound pulse 43 is transmitted from the ultrasound transducers 24 to 30. The ultrasound echo 44 from the observation target position 42 is received by the ultrasound transducers 24 to 30.

Figure 9:
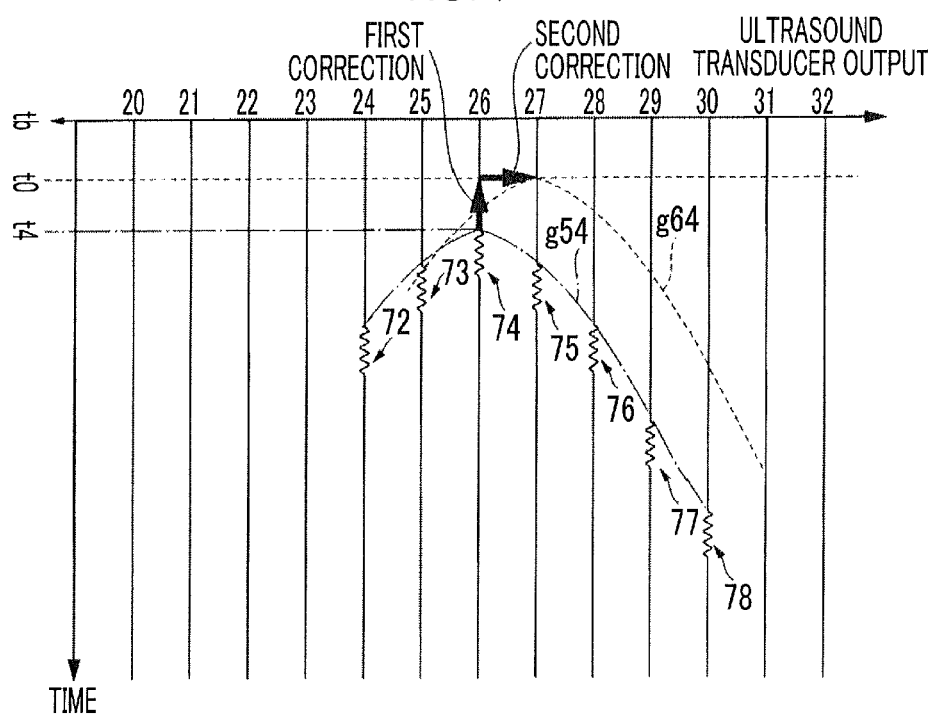
FIG. 9 shows an ultrasound echo signal.

Referring to FIG. 9, an ultrasound echo signal group g54 is obtained from the ultrasound transducers 24 to 30 in the same manner as in FIG. 3. As shown in FIG. 7, the ultrasound echo signal group g54 is also an envelope of ultrasound echo signals 72 to 78 output from the ultrasound transducers 24 to 30. In the same manner as described with reference to FIG. 2, the ultrasound echo signal 74 is first output from the ultrasound transducer 26 (time t4).

Referring to FIG. 10, it is assumed that ultrasound transducers to be driven are updated and the ultrasound pulse 43 is transmitted from the ultrasound transducers 25 to 31. The ultrasound echo 44 from the observation target position 42 is received by the ultrasound transducers 25 to 31.

Referring to FIG. 11, an ultrasound echo signal group g55 is obtained from the ultrasound transducers 25 to 31 in the same manner as in FIG. 2. As shown in FIG. 7, the ultrasound echo signal group g55 is also an envelope of ultrasound echo signals 73 to 79 output from the ultrasound transducers 25 to 31. The ultrasound echo signal 74 is first output from the ultrasound transducer 26 (time t5).

Referring to FIG. 1, the obtained ultrasound echo signals 69 to 79 are supplied to a receiving device 7. The ultrasound echo signals 69 to 79 or the like are amplified by the receiving device 7, and are converted into digital ultrasound echo signals by an A/D (analog/digital) conversion circuit 8. The ultrasound echo signals are supplied to an ultrasound echo data storage device 9 so as to be temporarily stored therein. The ultrasound echo signals are read from the ultrasound echo data storage device 9, and are input to an ultrasound echo data processing device 10.

In the ultrasound echo data processing device 10, among ultrasound echo signals (acoustic wave echo signals) that are output from ultrasound transducers (acoustic wave transducers) due to the ultrasound transducers (acoustic wave transducers) receiving the ultrasound echo (acoustic wave echo) of the observation target position 42 of the subject obtained based on the driving of the ultrasound transducers (acoustic wave transducers) by the control device 2 (a driving device), as shown in FIGS. 3, 5, 9, and 11, for an ultrasound echo signal (acoustic wave echo signal) with positional deviation in one direction (horizontal direction) between the focusing position 41 and the observation target position 42, the positional deviation is corrected according to the position of the ultrasound transducer to be driven (a positional deviation correction device).

As will be described later, the correction of positional deviation is to generate an ultrasound echo signal obtained in a case where it is assumed that the observation target position 42 is present on the extension line of the focusing position 41 and the ultrasound transducer 24 located at the center of the ultrasound transducers 21 to 27 that receive the ultrasound echo 44 from the observation target position 42.

Referring to FIG. 3, in the ultrasound echo data processing device 10, as shown in FIG. 7, first correction is performed in order to correct the delay time so that the ultrasound echo signal group g51 is output from the ultrasound transducer 26 at the time t0 as shown in FIG. 7, and second correction is performed in order to shift the apex of the ultrasound echo signal group g51 so that the one-direction positional deviation between the focusing position 41 and the observation target position 42 is eliminated. The positional deviation in one direction is a deviation between the focusing position 41 and the observation target position 42 in one direction. The correction of the positional deviation in one direction is to generate an ultrasound echo signal, which can be obtained in a case where there is no positional deviation in one direction, in a case where there is a positional deviation in one direction between the focusing position 41 and the observation target position 42 as shown in FIG. 2 (in a case where the focusing position 41 and the observation target position 42 are not present on a straight line in a direction perpendicular to the one direction). In the case shown in FIG. 2, the focusing position 41 and the observation target position 42 are shifted from each other by a distance of two ultrasound transducers in one direction. Accordingly, the ultrasound echo signal group g51 is shifted by the distance of two ultrasound transducers in a direction opposite to the one direction so that the deviation of the distance is eliminated. A combination of the first correction and the second correction is positional deviation correction (a positional deviation correction device). Therefore, as shown in FIG. 3, the ultrasound echo signal group g51 is corrected to an ultrasound echo signal group g61 as shown by the dotted line. Thus, in the ultrasound echo data processing device 10, among ultrasound echo signals (ultrasound echo data) that are output from the ultrasound transducers 21 to 27 due to the ultrasound transducers 21 to 27 receiving the ultrasound echo 44 of the observation target position 42 of the subject obtained based on the driving of the ultrasound transducers by the control device 2 (a driving device), for an ultrasound echo signal (ultrasound echo data) with positional deviation in one direction between the focusing position 41 and the observation target position 42, the positional deviation is corrected according to the position of the ultrasound transducer to be driven by the control device 2.

The delay time in the first correction can be calculated as follows.

Figure 12:
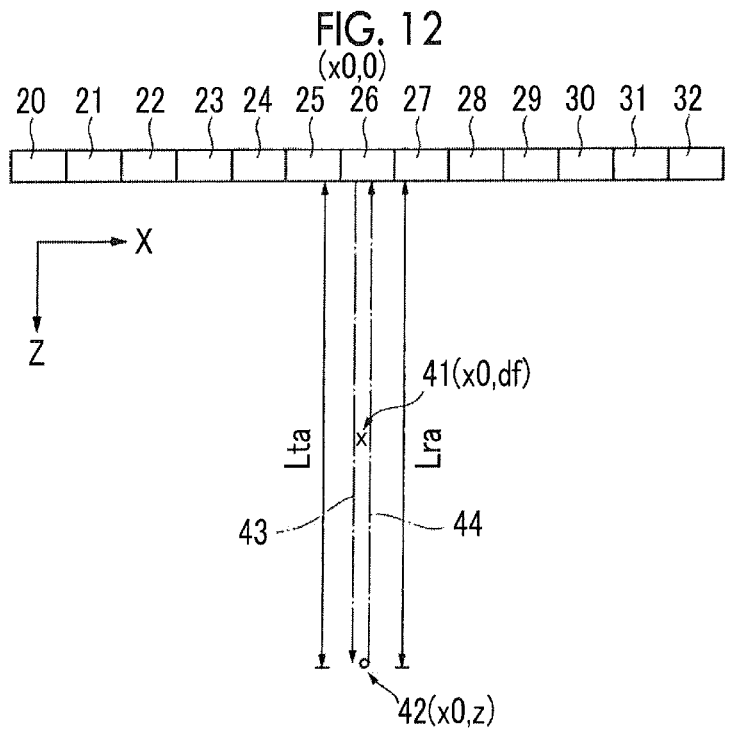
FIG. 12 shows the transmission of ultrasound pulses and the reception of ultrasound echoes.

FIG. 12 shows the ultrasound pulse 43 and the ultrasound echo 44 in a case where there is no positional deviation in one direction between the focusing position 41 and the observation target position 42 as shown in FIG. 6.

It is assumed that one direction is an X direction and a direction perpendicular to the one direction is a Z direction. It is assumed that the X and Z coordinates of the ultrasound transducer 26 located immediately above the focusing position 41 are (X, Z)=(x0, 0), the coordinates of the focusing position 41 are (X, Z)=(x0, df), and the coordinates of the observation target position 42 are (X, Z)=(x0, z). In a case where there is no positional deviation in one direction between the focusing position 41 and the observation target position 42, the length Lta of a transmission path until the ultrasound pulse 43 transmitted from the ultrasound transducer 26 reaches the observation target position 42 through the focusing position 41 is equal to the length Lra of a receiving path until the ultrasound echo 44 reflected from the observation target position 42 returns to the ultrasound transducer 26 from the observation target position 42. Accordingly, since Lta=Lra=z is satisfied, a propagation distance Lua obtained by adding up the propagation distance Lta of the ultrasound pulse 43 and the propagation distance Lra of the ultrasound echo 44 is Lua=Lta+Lra=2z. By dividing the propagation distance Lua obtained as described above by sound speed, the propagation time of the ultrasound pulse 43 and the ultrasound echo 44 in a case where there is no positional deviation is obtained.

Figure 13:
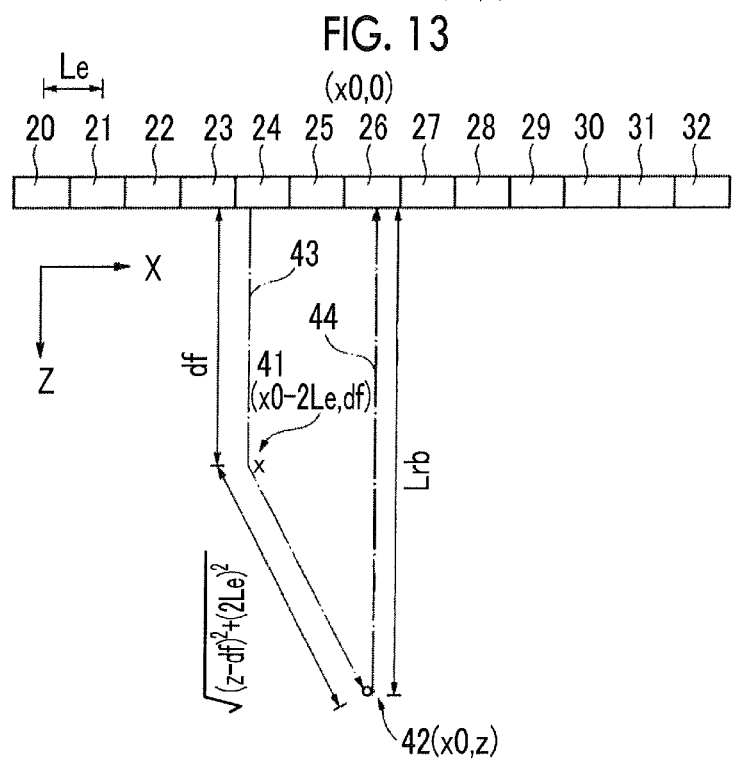
FIG. 13 shows the transmission of ultrasound pulses and the reception of ultrasound echoes.

FIG. 13 shows the ultrasound pulse 43 and the ultrasound echo 44 in a case where there is a positional deviation in one direction between the focusing position 41 and the observation target position 42 as shown in FIG. 2.

The focusing position 41 is shifted from the observation target position 42 by the distance between two ultrasound transducers in one direction. Assuming that the distance between ultrasound transducers is Le, the X and Z coordinates of the focusing position 41 are expressed by (X, Z)=(x0-2Le, df). The ultrasound pulse 43 transmitted from the ultrasound transducer 24 is transmitted to the observation target position 42 through the focusing position 41. The length Ltb of the transmission path of the ultrasound pulse 43 transmitted from the ultrasound transducer 24 is a sum of the distance df from the ultrasound transducer 24 to the focusing position 41 and a distance $\sqrt{(z-df)^2+(2Le)^2}$ from the focusing position 41 to the observation target position 42. In addition, the length Lrb of the receiving path until the ultrasound echo 44 reflected from the observation target position 42 reaches the ultrasound transducer 26 is Lrb=z. The propagation distance Lub obtained by adding up the propagation distance Ltb of the ultrasound pulse 43 and the propagation distance Lrb of the ultrasound echo 44 is Lub=Ltb+Lrb=$\sqrt{(z-df)^2+(2Le)^2}$+z. By dividing the propagation distance Lub obtained as described above by sound speed, the propagation time of the ultrasound pulse 43 and the ultrasound echo 44 in a case where there is a positional deviation is obtained.

From the difference between the propagation time in a case where there is no positional deviation and the propagation time in a case where there is a positional deviation, the delay time to be corrected in the first correction is calculated. It is needless to say that the delay time can be similarly calculated in the cases of positional deviation shown in FIGS. 4, 8, and 10 as well as in the case of positional deviation shown in FIG. 2.

Also for the ultrasound echo signal groups g52, g54, and g55 in which one-direction positional deviation occurs between the focusing position 41 and the observation target position 42 as in FIGS. 5, 9, and 11, positional deviation correction is performed by the ultrasound echo data processing device 10, and ultrasound echo signal groups g62, g64, and g65 after the positional deviation correction are obtained.

Then, the ultrasound echo signal groups g61, g62, g64, and g65 after the positional deviation correction and the ultrasound echo signal group g53 without positional deviation are superimposed by the ultrasound echo data processing device 10 so that the ultrasound echo signals output from the same ultrasound transducer are added up.

The superimposed ultrasound echo signals 69 to 79 are supplied to a phasing addition device 11.

Figure 14:
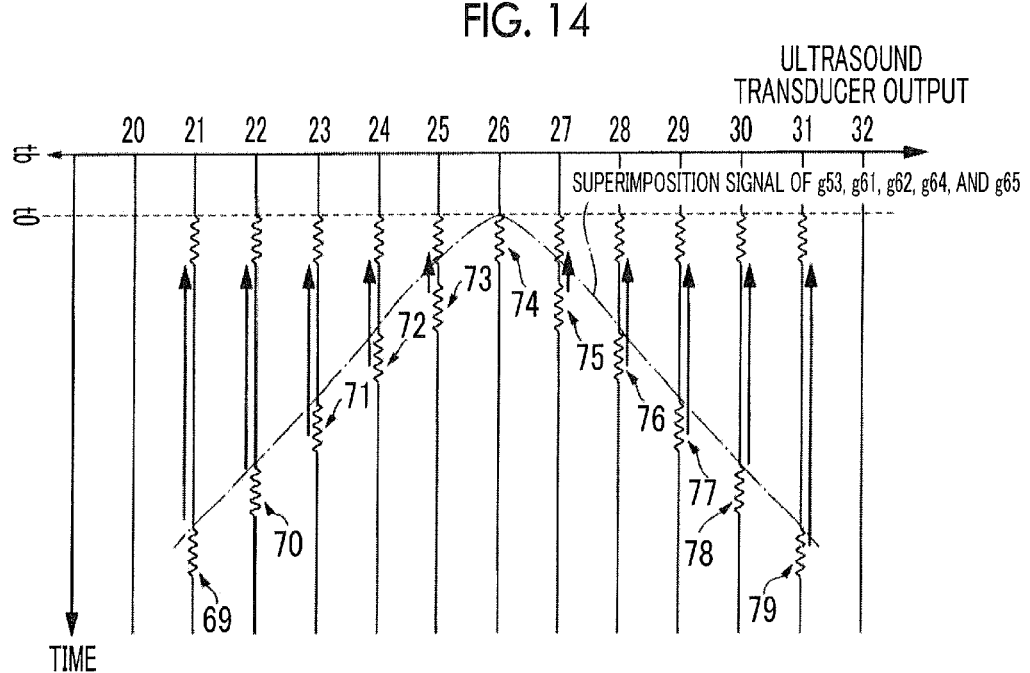
FIG. 14 shows a part of processing for phasing addition.
Figure 15:
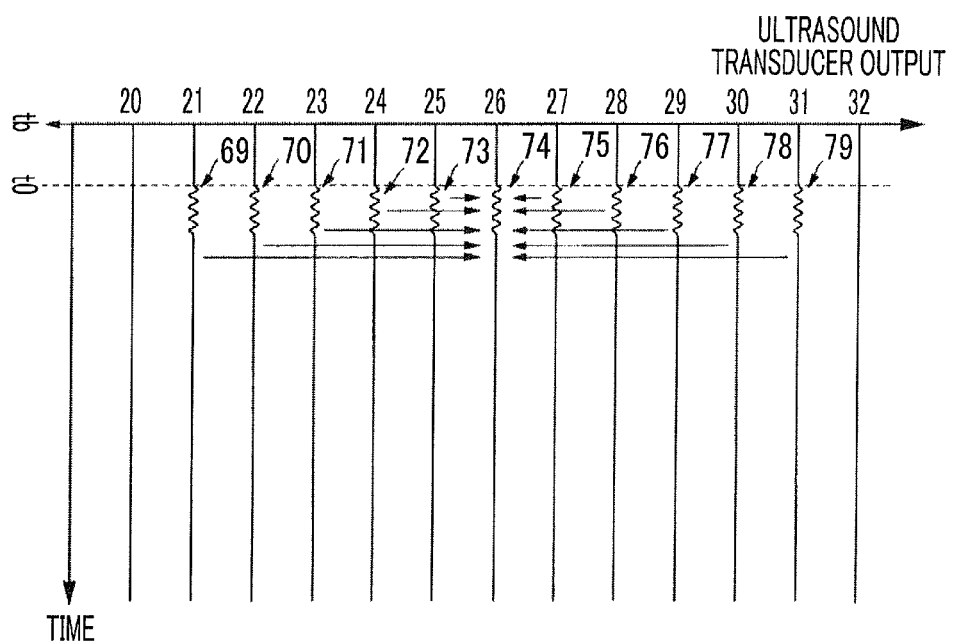
FIG. 15 shows a part of processing for phasing addition.

FIGS. 14 and 15 show a state in which the superimposed ultrasound echo signals 69 to 79 are phased and added.

Referring to FIG. 14, output time correction for the superimposed ultrasound echo signals 69 to 79 is performed by the phasing addition device 11 so that the output time of the superimposed ultrasound echo signals 69 to 79 becomes the same as the output timing of the ultrasound echo signal 74 that is first output from the ultrasound transducer 26 at time t0.

Then, referring to FIG. 15, the ultrasound echo signals 69 to 79 after the output time correction are phased and added by the phasing addition device 11 so as to be superimposed at the position of the ultrasound transducer 26 on the extension line of the observation target position 42. The S/N ratio is improved by performing phasing addition.

Similarly for the ultrasound echo signal groups g51, g52, g54, and g55 after the positional deviation correction and the delay time correction, phasing addition is also performed by the phasing addition device 11.

Referring to FIG. 1, the ultrasound echo signal after the phasing addition is supplied to a Doppler operation device (a Doppler operation means) 13 through a detection processing device 12. From the Doppler operation device 13, it is possible to obtain data indicating the speed in a case where there is a speed change at the observation target position 42.

Figure 16:
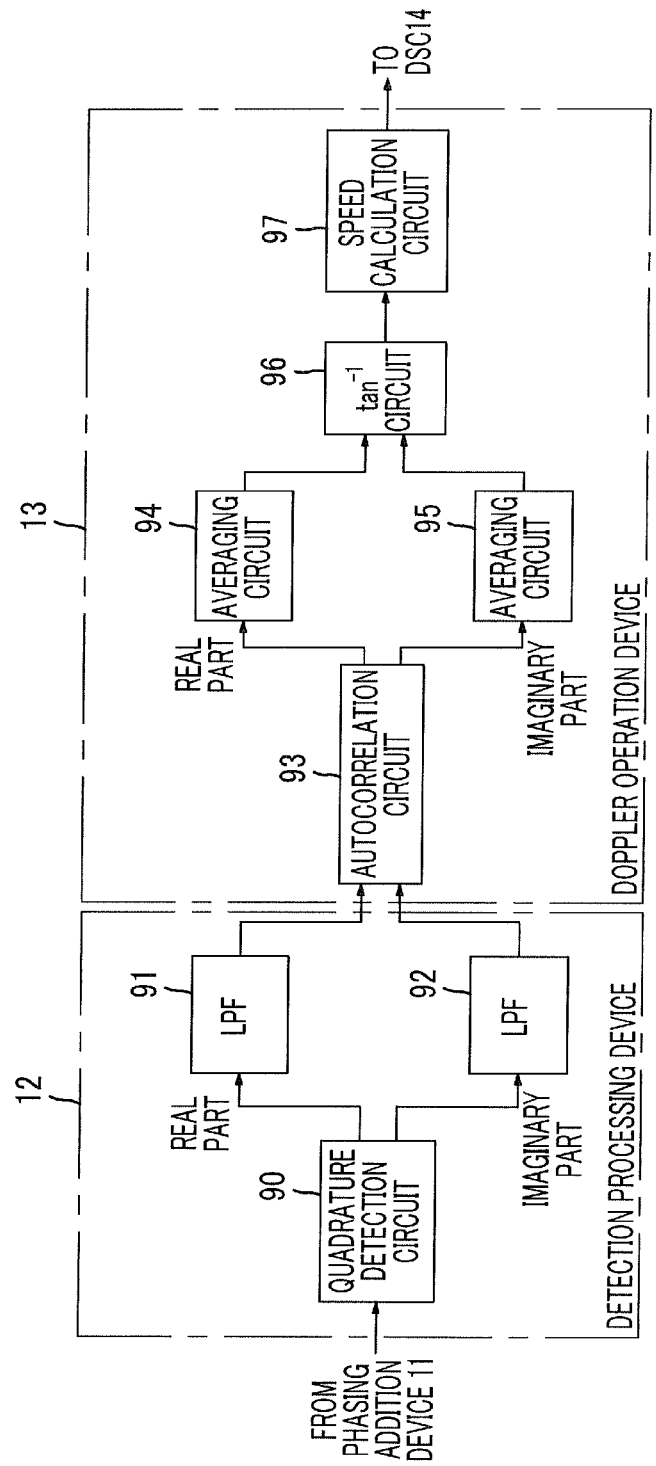
FIG. 16 is a block diagram showing the electrical configuration of a detection processing device and a Doppler operation device.

FIG. 16 is a block diagram showing the internal configuration of the detection processing device 12 and the Doppler operation device 13.

In order to obtain data indicating the speed, processing for transmitting ultrasound waves in the same direction of the subject with a time difference therebetween needs to be performed multiple times. This is because the data indicating the speed is calculated from the difference between the ultrasound echo signals of the observation target position 42 of the subject that are obtained due to the time difference. In the present embodiment, as shown in FIG. 6, in a case where the focusing position 41 is present between the observation target position 42 and the ultrasound transducer 26 located at the center of the ultrasound transducers 23 to 29 that receive the ultrasound echo 44, the ultrasound pulse 43 is transmitted eight times (several times) from the same ultrasound transducers 23 to 29. Accordingly, eight ultrasound echo signal groups g53 after phasing addition are obtained.

Figure 17:
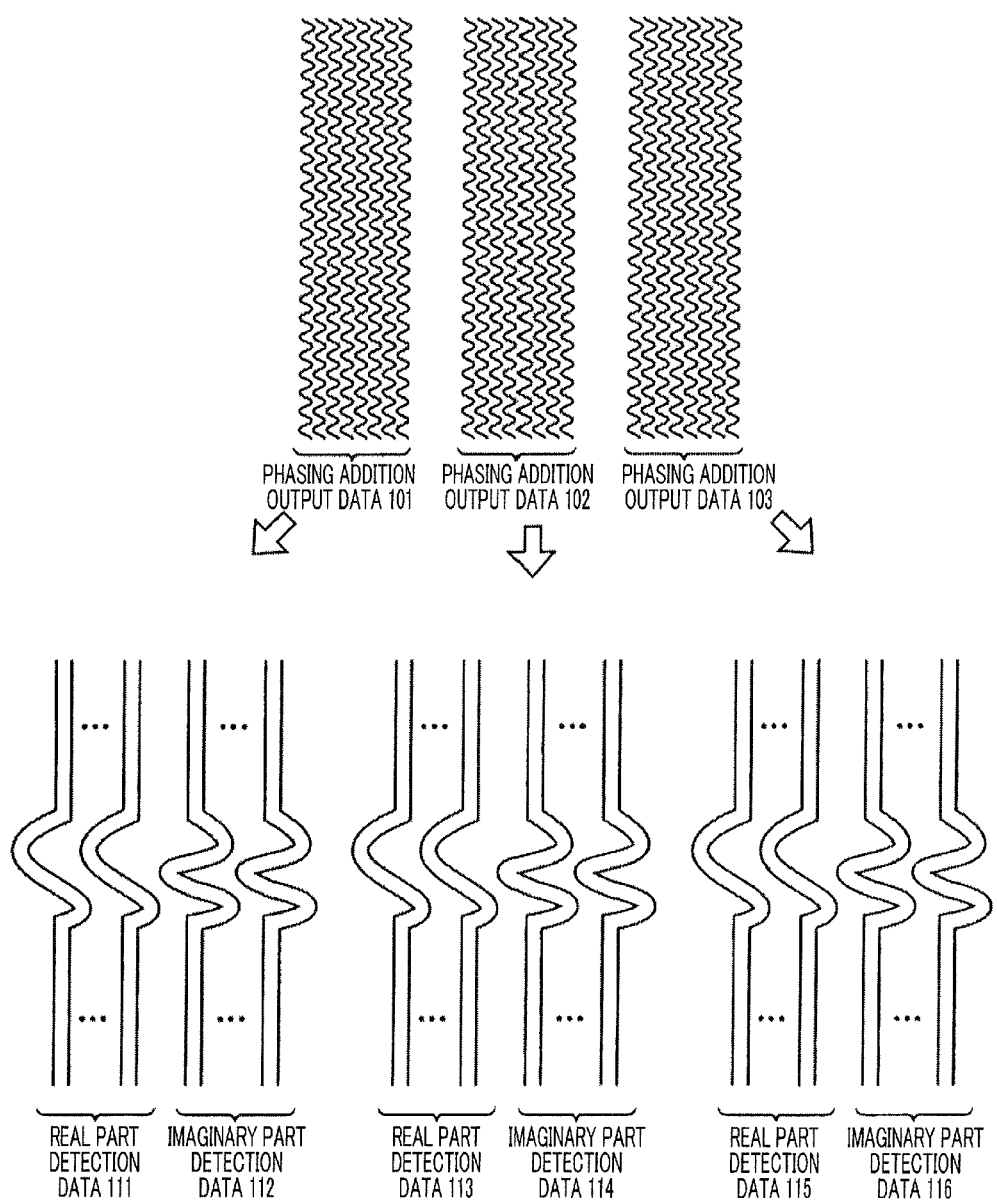
FIG. 17 shows phasing addition output data and detection data.

FIG. 17 shows ultrasound echo signals after phasing addition (phasing addition output data).

Phasing addition output data 101 indicates eight pieces of ultrasound echo data alter phasing addition that are obtained based on the ultrasound echo signal group g53 obtained as in FIG. 7.

In the present embodiment, also in a state in which the focusing position 41 is shifted to a side (left side) opposite to one direction from the observation target position 42 as shown in FIG. 4, the ultrasound pulse 43 is transmitted eight times from the same ultrasound transducers 22 to 28. Accordingly, eight ultrasound echo signal groups g52 after phasing addition are obtained.

Therefore, as shown in FIG. 17, eight pieces of phasing addition output data 102, which are obtained based on the eight ultrasound echo signal groups g52, are obtained.

In addition, also in a state in which the focusing position 41 is shifted to the one direction side (right side) from the observation target position 42 as shown in FIG. 8, the ultrasound pulse 43 is transmitted eight times from the same ultrasound transducers 24 to 30. Accordingly, eight ultrasound echo signal groups g54 after phasing addition are obtained.

Therefore, as shown in FIG. 17, eight pieces of phasing addition output data 103, which are obtained based on the eight ultrasound echo signal groups g54, are obtained.

In the present embodiment, a total of 24 pieces of phasing addition output data are obtained.

In a case where the observation target position 42 calculates a speed, in order to increase the accuracy of the calculated speed, it is necessary to increase the number of times to transmit the ultrasound pulse 43 to the observation target position 42. In contrast, as shown in FIG. 6, in the case of obtaining phasing addition output data only from ultrasound echo signals that are obtained in a case where there is no deviation in one direction between the focusing position 41 and the observation target position 42, it is necessary to transmit the ultrasound pulse 43 from the ultrasound transducers 23 to 29 24 times (not only in the case shown in FIG. 6 but also in the cases shown in FIGS. 4, 8, and the like, the ultrasound pulse 43 are transmitted 24 times). If the number of times of repeated transmission increases, a relatively long time is required. In the present embodiment, not only the ultrasound echo signals 71 to 77 obtained in a case where there is no deviation in one direction between the focusing position 41 and the observation target position 42 as shown in FIG. 6 but also the ultrasound echo signals 70 to 76 and 72 to 78 obtained in a case where the focusing position 41 and the observation target position 42 are shifted from each other in one direction as shown in FIGS. 4 and 8 are used. Accordingly, by transmitting the ultrasound pulse 43 from the ultrasound transducers 22 to 28 eight times as shown in FIG. 4, transmitting the ultrasound pulse 43 from the ultrasound transducers 23 to 29 eight times as shown in FIG. 6, and transmitting the ultrasound pulse 43 from the ultrasound transducers 24 to 30 eight times as shown in FIG. 8, a total of 24 pieces of phasing addition output data 101, 102, and 103 are obtained. This shortens the time until the speed is calculated.

The phasing addition output data 101 is input to a quadrature detection circuit 90 in the detection processing device 12. In the quadrature detection circuit 90, as shown in FIG. 17, eight pieces of real part detection data 111 and eight pieces of imaginary part detection data 112 are obtained. Similarly, the phasing addition output data 102 is also input to the quadrature detection circuit 90, and eight pieces of real part detection data 113 and eight pieces of imaginary part detection data 114 are obtained. Similarly, the phasing addition output data 103 is also input to the quadrature detection circuit 90, and eight pieces of real part detection data 115 and eight pieces of imaginary part detection data 116 are obtained.

The pieces of real part detection data 111, 113, and 115 are output from the detection processing device 12 after high-frequency components are removed by a low pass filter (LPF) 91. In addition, the pieces of imaginary part detection data 112, 114, and 116 are output from the detection processing device 12 after high-frequency components are removed by a low pass filter (LPF) 92.

The pieces of real part detection data 111, 113, and 115 output from the detection processing device 12 are input to an autocorrelation circuit 93 of the Doppler operation device 13. In the autocorrelation circuit 93, an autocorrelation operation is performed on the eight pieces of real part detection data 111. As a result, as shown in FIG. 18, seven pieces of real part autocorrelation output data 121 are obtained. Similarly, in the autocorrelation circuit 93, an autocorrelation operation is performed on the eight pieces of real part detection data 113 and the eight pieces of real part detection data 115. As a result, as shown in FIG. 18, seven pieces of real part autocorrelation output data 123 and seven pieces of real part autocorrelation output data 125 are obtained.

The pieces of imaginary part detection data 112, 114, and 116 output from the detection processing device 12 are input to the autocorrelation circuit 93 of the Doppler operation device 13. In the autocorrelation circuit 93, an autocorrelation operation is performed on the eight pieces of imaginary part detection data 112. As a result, as shown in FIG. 18, seven pieces of imaginary part autocorrelation output data 122 are obtained. Similarly, in the autocorrelation circuit 92, an autocorrelation operation is performed on the eight pieces of imaginary part detection data 114 and the eight pieces of imaginary part detection data 116. As a result, as shown in FIG. 18, seven pieces of imaginary part autocorrelation output data 124 and seven pieces of imaginary part autocorrelation output data 126 are obtained.

The pieces of real part autocorrelation output data 121, 123, and 125 output from the autocorrelation circuit 93 are input to an averaging circuit 94 to be averaged. The averaging circuit 94 may perform averaging processing so that the weighting of the real part autocorrelation output data 121 obtained based on the ultrasound echo signal group g53 without positional deviation between the focusing position 41 and the observation target position 42 as shown in FIG. 6 is higher than the weighting of the real part autocorrelation output data 123 and 125 obtained based on the ultrasound echo signal groups g52 and g54 with positional deviation between the focusing position 41 and the observation target position 42 as shown in FIGS. 4 and 8. This is because the real part autocorrelation output data 121 obtained based on the ultrasound echo signal group g53 without positional deviation between the focusing position 41 and the observation target position 42 as shown in FIG. 6 is more reliable than the real part autocorrelation output data 123 and 125 obtained based on the ultrasound echo signal groups g52 and g54 with positional deviation between the focusing position 41 and the observation target position 42 as shown in FIGS. 4 and 8.

The pieces of imaginary part autocorrelation output data 122, 124, and 126 output from the autocorrelation circuit 93 are input to an averaging circuit 95 to be averaged. Similar to the averaging circuit 94, the averaging circuit 95 may also perform averaging processing so that the weighting of the imaginary part autocorrelation output data 122 obtained based on the ultrasound echo signal group g53 without positional deviation between the focusing position 41 and the observation target position 42 as shown in FIG. 6 is higher than the weighting of the imaginary part autocorrelation output data 124 and 126 obtained based on the ultrasound echo signal groups g52 and g54 with positional deviation between the focusing position 41 and the observation target position 42 as shown in FIGS. 4 and 8.

Imaginary part autocorrelation output data obtained by the averaging in the averaging circuit 94 and real part autocorrelation output data obtained by the averaging in the averaging circuit 95 are input to an arctangent ($\tan^{-1}$) circuit 96. Accordingly, as shown in the lower part of FIG. 13, data (Doppler shift signal) 131 indicating the Doppler frequency is obtained. The data indicating the Doppler frequency is supplied to a speed calculation circuit 97, so that the data indicating the speed is obtained in the observation target position 42. The data indicating the speed becomes is input to a digital scan converter (DSC) 14 as output data of the Doppler operation device 13.

The DSC 14 performs raster conversion into image data according to the normal scan method of television signals. The image data output from the DSC 14 is subjected to image processing, such as gradation processing, by an image generating device 15. Image data output from the image generating device 15 is supplied to a display control device 17, and a color-mode ultrasound image is displayed on the display screen of a display device 18. The image data output from the image generating device 15 is also supplied to an image memory 16, and the image data indicating an ultrasound image is stored in the image memory 16. By supplying the image data stored in the image memory 16 to the display control device 17, an ultrasound image is displayed on the display screen of the display device 18.

In the embodiment described above, in each of the states shown in FIGS. 4, 6, and 8, the ultrasound pulse 43 is transmitted eight times. However, the number of times to transmit the ultrasound pulse 43 is not limited to eight times if a plurality of ultrasound echo signals can be obtained from the observation target position 42 based on the ultrasound pulses 43 transmitted at different times. For example, it is also possible to generate a Doppler shift signal using the ultrasound echo signal group g53 shown in FIG. 6 and the ultrasound echo signal of at least one of the ultrasound echo signal group g51, g52, g54, or g55 shown in FIG. 2, 4, 8, or 10. In addition, a Doppler shift signal may be generated by performing an autocorrelation operation on the ultrasound echo signal without positional deviation and the ultrasound echo signal obtained by performing positional deviation correction for the ultrasound echo signal groups g52 and g54 with the smallest positional deviation between the focusing position 41 and the observation target position 42 as shown in FIGS. 4 and 8. However, a Doppler shift signal may also be generated by performing an autocorrelation operation using the ultrasound echo signal obtained by performing positional deviation correction for the ultrasound echo signal groups g51 and g55 with relatively large positional deviation between the focusing position 41 and the observation target position 42 as shown in FIGS. 2 and 8. Although the number of ultrasound transducers to transmit the ultrasound pulse 43 is seven in the embodiment described above, the number of ultrasound transducers may be other numbers, for example, one, without being limited to seven.

Figure 19:
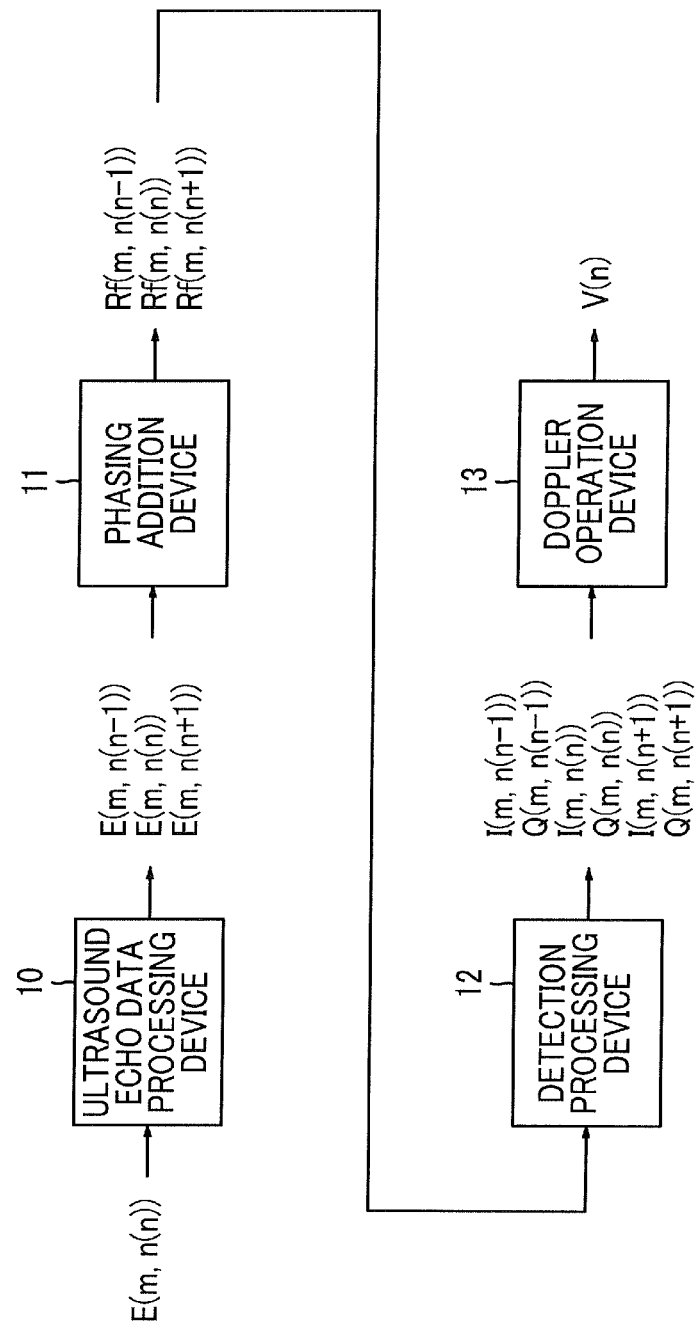
FIG. 19 shows how data indicating the speed is generated from the ultrasound echo signal.

FIG. 19 shows a flow until the data indicating the speed of the observation target position 42 is obtained.

An ultrasound echo signal in the m-th transmission, among transmissions of the ultrasound pulse 43 from the same ultrasound transducer, in a case where the number of order of the central ultrasound transducer of a plurality of ultrasound transducers for transmitting the ultrasound pulse 43 is n (in a case where there is one ultrasound transducer for transmitting the ultrasound pulse 43, the number of order of the ultrasound transducer) is assumed to be E(m, n(n)). As described above, in a case where the number of transmissions of the ultrasound pulse 43 from the ultrasound probe 6 (ultrasound transducer) is M (in the embodiment described above, M=8) and the number of ultrasound transducers is N, ultrasound echo signals of M×N are stored in the ultrasound echo data storage device 9. Here, m=1–M, and n=1 to N.

The ultrasound echo signal E(m, n(n)) in a case where the ultrasound pulse 43 is transmitted from an ultrasound transducer in a case where the n-th ultrasound transducer is located at the center is read from the ultrasound echo data storage device 9. From the ultrasound echo data storage device 9, the ultrasound echo signal group g53 shown in FIG. 6 is read. In addition, ultrasound echo signals in a case where ultrasound waves are transmitted from ultrasound transducers on both sides of the n-th ultrasound transducer, that is, from (n−1)-th and (n+1)-th ultrasound transducers, are also read from the ultrasound echo data storage device 9. From the ultrasound echo data storage device 9, the ultrasound echo signal groups g52 and g54 shown in FIGS. 5 and 9 are read. The read ultrasound echo signal group is input to the ultrasound echo data processing device 10, and delay time correction is performed for the ultrasound echo signal group g53 shown in FIG. 7 as described above. As a result, the ultrasound echo signal E(m, n(n)) after the delay time correction is obtained. In addition, positional deviation correction and delay time correction are performed for the ultrasound echo signal groups g52 and g54 shown in FIGS. 5 and 9, so that ultrasound echo signals E(m, n(n−1)) and E(m, n(n+1)) are obtained.

The ultrasound echo signals E(m, n(n)), E(m, n(n−1)), and E(m, n(n+1)) are supplied to the phasing addition device 11 as described above. As shown in FIG. 19, phasing addition is performed to obtain ultrasound echo signals Rf(m, n(n)) 101, Rf(m, n(n−1)) 102, and Rf(m, n(n+1)) 103 after the phasing addition.

The ultrasound echo signals Rf(m, n(n)) 101, Rf(m, n(n−1)) 102, and Rf(m, n(n+1)) 103 after the phasing addition are supplied to the detection processing device 12 as described above. The detection processing device 12 performs quadrature detection as described above, thereby obtaining real part detection data I(m, n(n)) 111, I(m, n(n−1)) 113, and I(m, n(n+1)) 115 and imaginary part detection data Q(m, n(n)) 112, Q(m, n(n−1)) 114, and Q(m, n(n+1)) 116 (refer to FIG. 17).

The real part detection data I(m, n(n)) 111, I(m, n(n−1)) 113, and I(m, n(n+1)) 115 and the imaginary part detection data Q(m, n(n)) 112, Q(m, n(n−1)) 114, and Q(m, n(n+1)) 116 after the quadrature detection are supplied to the Doppler operation device 13, and data V(n) indicating the speed is obtained.

Although the embodiment described above is based on the color mode, the ultrasound diagnostic apparatus 1 can also display a B-mode tomographic image.

In the case of displaying a B-mode tomographic image, output data from the detection processing device 12 is supplied to the digital scan converter (DSC) 14 after simply passing through the Doppler operation device 13. The DSC 14 performs raster conversion into image data according to the normal scan method of television signals. The image data output from the DSC 14 is subjected to image processing, such as gradation processing, by an image generating device 15. The image data output from the image generating device 15 is supplied to the display control device 17, and an ultrasound image is displayed on the display screen of the display device 18. The image data output from the image generating device 15 is also supplied to an image memory 16, and the image data indicating an ultrasound image is stored in the image memory 16. By supplying the image data stored in the image memory 16 to the display control device 17, an ultrasound image is displayed on the display screen of the display device 18.

In the present embodiment, it is also possible to display an image obtained by combining a B-mode image and a color-mode image.

FIG. 20 shows how to generate a composite image from a B-mode image and a color-mode image.

A B-mode image 140 is obtained, and image data indicating the B-mode image 140 is temporarily stored in the image memory 16. In the B-mode image 140, an image 142 of blood vessels and images 141 and 143 of the periphery of the blood vessels appear. The B-mode image 140 is a black-and-white image. A color-mode image 145 shows a blood flow at a speed, and is a color image. The density of color changes according to the speed.

The B-mode image 140 and the color-mode image 145 are combined in the image memory 16, thereby obtaining a composite image 150. The composite image 150 is displayed on the display screen of the display device 18.

What is claimed is:

1. An acoustic wave diagnostic apparatus, comprising:
   an acoustic wave probe in which a plurality of acoustic wave transducers are arranged in at least one direction;
   a first processor circuitry for performing processing for transmitting acoustic waves, which converge on a focusing position, in a subject from the acoustic wave transducers to be driven while sequentially updating the acoustic wave transducers to be driven;
   a second processor circuitry for directly correcting positional deviation of the one direction according to a position of each of the acoustic wave transducers driven by the first processor circuitry, for an acoustic wave echo signal with positional deviation in the one direction in which the plurality of acoustic wave transducers are arranged, between the focusing position and an observation target position of the subject among acoustic wave echo signals that are output from the acoustic wave transducers due to the acoustic wave transducers receiving acoustic wave echoes of the observation target position of the subject obtained based on the driving of the acoustic wave transducers by the first processor circuitry;
   a Doppler processor circuitry for generating a Doppler shift signal by performing an autocorrelation operation on the acoustic wave echo signal, for which the positional deviation of the one direction has been corrected by the second processor, and the acoustic wave echo signal without the positional deviation of the one direction, and
   wherein the Doppler processor circuitry generates the Doppler shift signal by increasing a weighting of the plurality of acoustic wave echo signals without the positional deviation and calculating a weighted average of an autocorrelation operation result of the plurality of acoustic wave echo signals, for which the positional deviation has been corrected by the second processor circuitry, and an autocorrelation operation result of the plurality of acoustic wave echo signals without the positional deviation.

2. The acoustic wave diagnostic apparatus according to claim 1,
   wherein the Doppler processor circuitry generates the Doppler shift signal from an average of an autocorrelation operation result of the plurality of acoustic wave echo signals, for which the positional deviation has been corrected by the second processor circuitry, and an autocorrelation operation result of the plurality of acoustic wave echo signals without the positional deviation.

3. The acoustic wave diagnostic apparatus according to claim 2,
   wherein the Doppler processor circuitry generates the Doppler shift signal from a weighted average of an autocorrelation operation result of the plurality of acoustic wave echo signals, for which the positional deviation has been corrected by the second processor circuitry, and an autocorrelation operation result of the plurality of acoustic wave echo signals without the positional deviation.

4. A control method of an acoustic wave diagnostic apparatus comprising an acoustic wave probe in which a plurality of acoustic wave transducers are arranged in at least one direction, comprising:
   causing a first processor circuitry to perform processing for transmitting acoustic waves, which converge on a focusing position, in a subject from the acoustic wave transducers to be driven while sequentially updating the acoustic wave transducers to be driven;
   causing a second processor circuitry to directly correct positional deviation of the one direction according to a position of each of the acoustic wave transducers driven by the first processor circuitry, for an acoustic wave echo signal with positional deviation in the one direction in which the plurality of acoustic wave transducers are arranged, between the focusing position and an observation target position of the subject among acoustic wave echo signals that are output from the acoustic wave transducers due to the acoustic wave transducers receiving acoustic wave echoes of the observation target position of the subject obtained based on the driving of the acoustic wave transducers by the first processor circuitry; and
   causing Doppler processor circuitry to generate a Doppler shift signal by performing an autocorrelation operation on the acoustic wave echo signal, for which the positional deviation of the one direction has been corrected by the second processor, and the acoustic wave echo signal without the positional deviation of the one direction, and
   wherein the Doppler processor circuitry generates the Doppler shift signal by increasing a weighting of the plurality of acoustic wave echo signals without the positional deviation and calculating a weighted average of an autocorrelation operation result of the plurality of acoustic wave echo signals, for which the positional deviation has been corrected by the second processor circuitry, and an autocorrelation operation result of the plurality of acoustic wave echo signals without the positional deviation.

5. The control method of an acoustic wave diagnostic apparatus according to claim 4,
   wherein the Doppler processor circuitry generates the Doppler shift signal from a weighted average of an autocorrelation operation result of the plurality of acoustic wave echo signals, for which the positional deviation has been corrected by the second processor circuitry, and an autocorrelation operation result of the plurality of acoustic wave echo signals without the positional deviation.

6. The control method of an acoustic wave diagnostic apparatus according to claim 4,
   wherein the Doppler processor circuitry generates the Doppler shift signal by performing an autocorrelation operation on each of the plurality of acoustic wave echo signals without the positional deviation and the plurality of acoustic wave echo signals, for which the positional deviation has been corrected by the second processor circuitry, among the plurality of acoustic wave echo signals with a smallest positional deviation.

7. The control method of an acoustic wave diagnostic apparatus according to claim 4, further comprising:
   delay time correction device for correcting a time difference between transmission of the acoustic waves by the acoustic wave transducers and reception of the acoustic wave echoes by the acoustic wave transducers, which occurs based on positions of the acoustic wave transducers in the acoustic wave probe, wherein the Doppler processor circuitry generates the Doppler shift signal for the acoustic wave echo signal for which a delay time has been corrected by the delay time correction device.

8. The acoustic wave diagnostic apparatus according to claim 1, wherein the Doppler processor circuitry generates the Doppler shift signal by increasing a weighting of the plurality of acoustic wave echo signals without the positional deviation as to the plurality of acoustic wave echo signals for which the positional deviation has been corrected and the plurality of acoustic wave echo signals without the positional deviation obtained from the acoustic wave echoes from the same subject.

9. The acoustic wave diagnostic apparatus according to claim 1, wherein the Doppler processor circuitry generates the Doppler shift signal by real part auto correlation output data and imaginary part detection data are separated, averaged separately, and applied to an arc tangent circuit.

* * * * *